US006535574B1

(12) United States Patent
Collins et al.

(10) Patent No.: US 6,535,574 B1
(45) Date of Patent: Mar. 18, 2003

(54) PATIENT POSITIONING SYSTEM EMPLOYING SURFACE PHOTOGRAMMETRY AND PORTAL IMAGING

(75) Inventors: William F. Collins, Clayton, CA (US); Ali Bani-Hashemi, Walnut Creek, CA (US); Michelle Marie Svatos, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/004,206

(22) Filed: Nov. 1, 2001

(51) Int. Cl.[7] .................................................. A61N 5/10
(52) U.S. Cl. .............................. 378/65; 378/20; 378/205
(58) Field of Search ............................. 376/65, 20, 205, 376/206

(56) References Cited

U.S. PATENT DOCUMENTS 6,222,544 B1    4/2001    Tarr et al.

FOREIGN PATENT DOCUMENTS

WO    WO 99/40846    8/1999

OTHER PUBLICATIONS

L.M. Girouard et al., "Automatic setup deviation measurements with electronic portal images for pelvic fields", Medical Physics, vol. 35, No. 7, Jul. 1998.

*Primary Examiner*—Craig E. Church

(57) ABSTRACT

A system includes acquistion of first data representing a three-dimensional surface of at least a portion of a patient'body while the patient is in a first position substantially maintained in preparation for radiation treatment, acquistion of an image of a first internal portion of the patient's body while the patient is substantially in the first position, and determination of whether the patient is properly positioned for radiation treatment based on the first data and the image.

26 Claims, 9 Drawing Sheets

PATIENT POSITIONING SYSTEM EMPLOYING SURFACE PHOTOGRAMMETRY AND PORTAL IMAGING

CROSS-REFERENCE TO RELATED APPLICATIONS

This application is related to commonly owned U.S. patent application Ser. No. 10/004,363, filed Nov. 1, 2001 (on even date herewith), for "PATIENT POSITIONING SYSTEM EMPLOYING SURFACE PHOTOGRAMMETRY", the contents of which are incorporated by reference in their entirety for all purposes.

BACKGROUND OF THE INVENTION

1. Field of the Invention

The present invention relates generally to radiation treatment, and more particularly to facilitating patient positioning during such treatment.

2. Description of the Related Art

Conventional radiation treatment typically involves directing a radiation beam at a tumor in a patient to deliver a predetermined dose of therapeutic radiation to the tumor according to an established treatment plan. A suitable radiation treatment device is described in U.S. Pat. No. 5,668,847, issued Sep. 16, 1997 to Hernandez, the contents of which are incorporated herein for all purposes.

Healthy tissue and organs are often in the treatment path of the radiation beam during radiation treatment. The healthy tissue and organs must be taken into account when delivering a dose of radiation to the tumor, thereby complicating determination of the treatment plan. Specifically, the plan must strike a balance between the need to minimize damage to healthy tissue and organs and the need to ensure that the tumor receives an adequately high dose of radiation. In this regard, cure rates for many tumors are a sensitive function of the radiation dose they receive.

Treatment plans are therefore designed to maximize radiation delivered to a target while minimizing radiation delivered to healthy tissue. However, a treatment plan is designed assuming that relevant portions of a patient will be in a particular position during treatment. If the relevant portions are not positioned exactly as required by the treatment plan, the goals of maximizing target radiation and minimizing healthy tissue radiation may not be achieved. More specifically, errors in positioning the patient can cause the delivery of low radiation doses to tumors and high radiation doses to sensitive healthy tissue. The potential for misdelivery increases with increased positioning errors.

Due to the foregoing, treatment plans are designed under the assumption that positioning errors may occur that may result in misdelivery of radiation. Treatment plans compensate for this potential misdelivery by specifying lower doses or smaller beam shapes (e.g., beams that do not radiate edges of a tumor) than would be specified if misdelivery was not expected. Such compensation may decrease as margins of error in patient positioning decrease.

Current radiation treatment devices provide sophisticated control over radiation delivery to a patient site. Specifically, these devices allow a therapist to target a tumor with Intensity-Modulated RadioTherapy (IMRT) treatments, Conformal Radiation Treatments (CRT) and composite radiation beam distributions. However, as described above, the full effectiveness of such features cannot be achieved without a system providing accurate patient positioning.

When used in conjunction with conventionally-designed treatments, more accurate positioning reduces the chance of harming healthy tissue. More accurate patient positioning also allows the use of more aggressive treatments. Specifically, if a margin of error in patient positioning is known to be small, treatment may be designed to safely radiate a greater portion of a tumor with higher doses than in scenarios where the margin of error is larger.

Modern radiation treatments provide the delivery of multiple radiation beams during the course of treatment. A treatment is divided into multiple fractions, with each fraction being delivered to a patient according to a periodic schedule such as weekly or the like. Each fraction consists of multiple segments, with each segment specifying a particular beam type, beam shape, dose, treatment device position, and delivery time. Of course, two segments of a fraction need not differ in each of the above factors.

During a treatment fraction, adjustments must be made after each segment to the treatment device and to the patient position. These adjustments are often time-consuming, because most radiation therapy devices are located within vaults constructed with thick concrete walls and thick doors that can take 30 seconds to open and close. Therefore, it can take a significant amount of time after a segment is completed for an operator to enter the room, make the necessary adjustments, leave the room, and operate the radiation treatment device to deliver the next segment.

The recently-developed SIMTEC™ Delivery System provides a more practical way to provide intensity-modulated treatments by providing a fast sequential delivery technique. By observing visual icons at the control console, the operator can constantly monitor and track every field being delivered. When a treatment device, or linear accelerator (Linac), is equipped with SIMTEC for a sequential delivery process, the need for walking into and out of the treatment room to rotate a gantry, move a treatment table, or to remove or place blocks or wedges is reduced. As a result, treatment times and associated expenses are reduced.

SUMMARY OF THE INVENTION

Some embodiments of the present invention provide a system, method, apparatus, and means to acquire first data representing a three-dimensional surface of at least a portion of a patient's body while the patient is in a first position substantially maintained in preparation for radiation treatment, to acquire an image of a first internal portion of the patient's body while the patient is substantially in the first position, and to determine whether the patient is properly positioned for radiation treatment based on the first data and the image.

In some embodiments, the present invention further provides acquisition, prior to acquiring the first data, of second data representing a three-dimensional surface of at least a portion of the patient's body while the patient is in a second position, and determination of whether the patient is properly positioned for radiation treatment based on the first data, the second data and the image.

According to some embodiments, the present invention may instead further provide automatic delivery of a first segment of a sequential radiation treatment plan to the patient, automatic adjustment of a position of the patient relative to a radiation treatment device according to the sequential radiation treatment plan after the first segment is delivered, automatic adjustment of a delivery configuration of the radiation treatment device according to the sequential radiation treatment plan, and automatic delivery of a second segment of the sequential radiation treatment plan to the patient.

The present invention is not limited to the disclosed preferred embodiments, however, as those skilled in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein.

DETAILED DESCRIPTION

The following description is provided to enable any person skilled in the art to make and use the invention and sets forth the best modes contemplated by the inventors for carrying out the invention. Various modifications, however, will remain readily apparent to those in the art.

Figure 1:
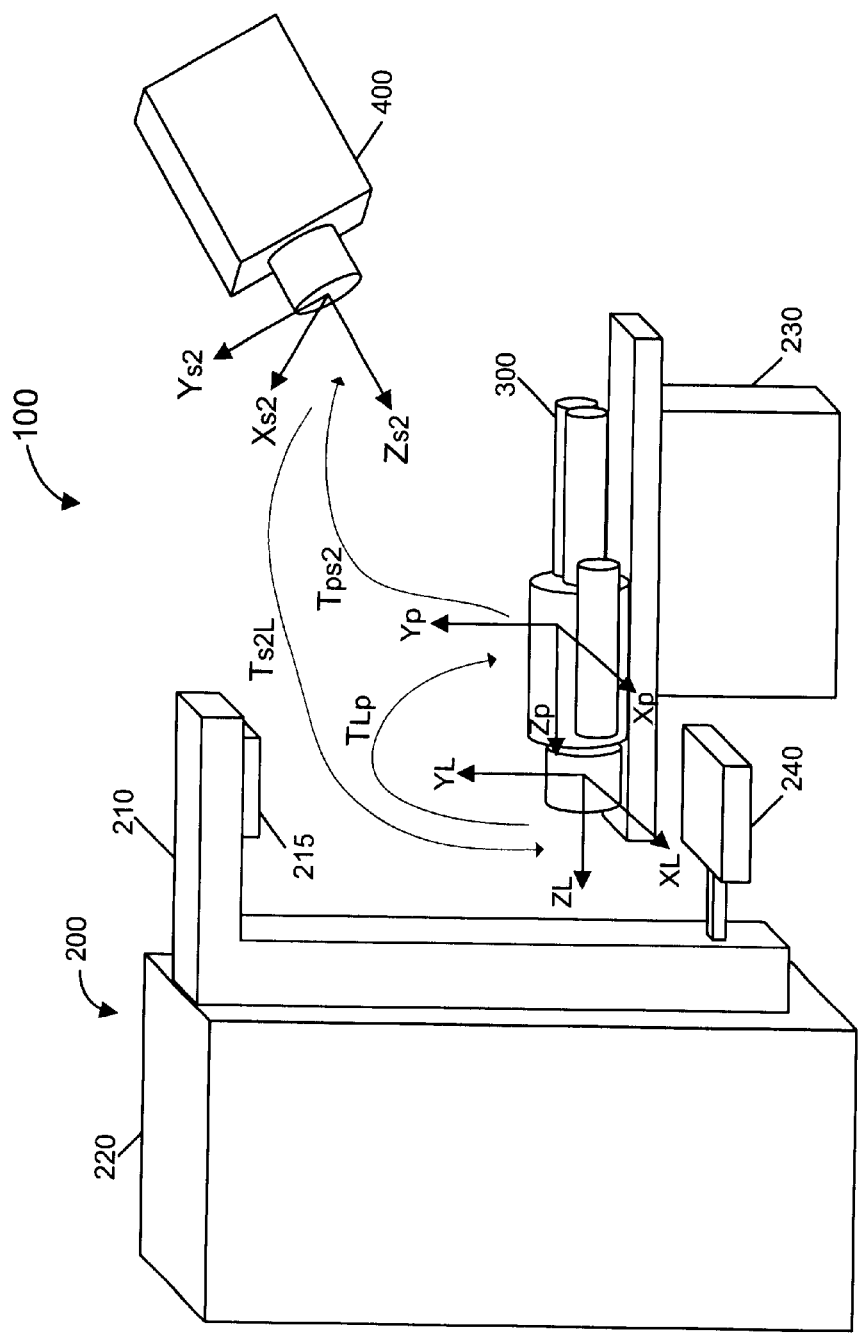
FIG. 1 is diagram illustrating a radiation treatment room according to some embodiments of the present invention.

Turning to the drawings, FIG. 1 illustrates Linac room 100 according to some embodiments of the invention. Linac room 100 includes Linac 200, patient 300, and surface imager 400. The coordinate axes shown in FIG. 1 and the arrows connecting the axes will be described below and will therefore be ignored in the present discussion of the elements of FIG. 1.

As shown, Linac 200 includes gantry 210, base 220, Linac table 230 and portal imager 240. Gantry 210 contains treatment head 215 from which a beam of radiation is emitted. The beam may comprise electron, photon or any other type of detectable radiation. Gantry 210 can be swiveled around a horizontal axis of rotation during radiation treatment so as to provide different beam angles and radiation distributions with respect to patient 300 without having to move patient 300. According to some embodiments of the invention, gantry 210, treatment head 215, Linac table 230 and portal imager 240 are integratedly controlled to provide radiation treatment according to a sequential treatment plan. As a result, these elements may be used to automatically deliver successive treatment segments to a patient during a treatment fraction.

Portal imager 240 is used to acquire an image of an internal portion of patient 300 for verification and recordation of a treatment field. Portal imager 240 may be attached to gantry 210 in any manner that allows it to be controllably placed under patient 300. In some embodiments, portal imager 240 is a flat-panel imaging device using solid-state amorphous silicon sensors. The RID 1640, offered by PerkinElmer®, Inc. of Fremont, Calif., is one suitable device. Portal imager 240 may be formed with a plurality of detector elements formed in a two dimensional array. In some embodiments, each detector element (or "pixel") in the array is a solid-state sensor, such as a solid-state amorphous silicon sensor. Operation of portal imager 240 may result in the capture of a two-dimensional image. The captured image is then corrected to create an image of the electron field, thereby allowing quick and efficient verification of the treatment field including patient anatomy, position and the field shape.

Many radiation treatment devices utilize portal imaging techniques to verify and record a patient isocenter prior to delivery of a radiation beam. The patient isocenter is the center of the tumor or other target to which therapeutic radiation is to be delivered. Portal images are images of the patient portal through which the radiation passes. These images can be taken before or after treatment to ascertain that the patient position, as well as the beam shape, conform to a desired treatment plan. According to some embodiments of the invention, elements of Linac 200 are automatically controlled so as to conform the position to the treatment plan in a case that it is ascertained that the position does not so conform.

Surface imager 400 acquires a range image representing a three-dimensional surface within Linac room 100. A range image is a picture in which each pixel value encodes not the intensity of light reflected in a certain direction but rather the distance (or range) of the nearest surface in that direction. The surface preferably includes at least a portion of patient 300. More specifically, the acquired surface data may be used in conjunction with surface data acquired during a Computed Tomography (CT) scan to substantially duplicate, on Linac table 230, a position of at least a portion of a patient's body that was maintained during the CT scan.

Surface imager 400 may acquire the data of the range image using any suitable technique, such as stereo video acquisition or time-of-flight laser detection. In the present description, surface imager 400 acquires three-dimensional surface data by projecting a light pattern onto a surface and by sensing how the light pattern coats the surface. Of course, data acquired by surface imager 400 need not be in a range data format; any format usable to represent three-dimensional surface data will suffice.

In an example according to some embodiments of the invention, details of a treatment plan segment are transmitted to Linac 200. The details include data representing a patient position, a beam type, a beam intensity, a beam shape, a gantry position and a portal imager position. Based on the received beam shape, collimator plates or leaves mounted between a radiation source within treatment head 215 and patient 300 are moved to delimit (conform) the field. In this regard, collimator plates or leaves of a beam-shielding device within head 215 are substantially impervious to the emitted radiation. Non-targeted areas of the body such as healthy tissue are therefore subject to as little radiation as possible and preferably to none at all. Also, the plates or leaves are movable such that the distribution of radiation over the field need not be uniform (one region can be given a higher dose than another).

Gantry 210 and table 230 are automatically adjusted based on the segment details. Surface imager 400 then acquires data representing a three-dimensional surface of patient 300, and portal imager 240 acquires an image of an internal portion of patient 300. Based on the position specified in the segment details, it is determined whether the acquired image and data indicate that the patient is properly positioned. If not, gantry 210 and table 230 are automatically adjusted to move the patient into the proper position and the position is rechecked. Once the position is proper, the specified radiation beam is delivered.

During radiation delivery, the radiation beam is trained on the Linac isocenter, located at the intersection of axes $X_L$, $Y_L$ and $Z_L$ of FIG. 1. Accordingly, patient 300 is preferably positioned so that the center of an area to be radiated, or the patient isocenter (located at the intersection of axes $X_p$, $Y_p$ and $Z_p$), is located at the Linac isocenter. Therefore, the position of patient 300 shown in FIG. 1 is not optimal for delivering treatment. More specifically, patient 300 should be positioned prior to treatment so that the patient isocenter and the Linac isocenter coincide. After radiation delivery, details of a next segment are received and the segment is automatically executed as described above.

Accordingly, in some embodiments, the elements of room 100 operate to acquire data representing a three-dimensional surface of at least a portion of a patient's body while the patient is in a first position substantially maintained for radiation treatment, and to acquire an image of a first internal portion of the patient's body while the patient is substantially in the first position. Based on the data and the image, it may be determined whether the patient is properly positioned for radiation treatment. These features advantageously allow high accuracy in patient positioning, thereby reducing risk to healthy tissue during radiation delivery and enabling usage of more aggressive treatments.

Figure 2:
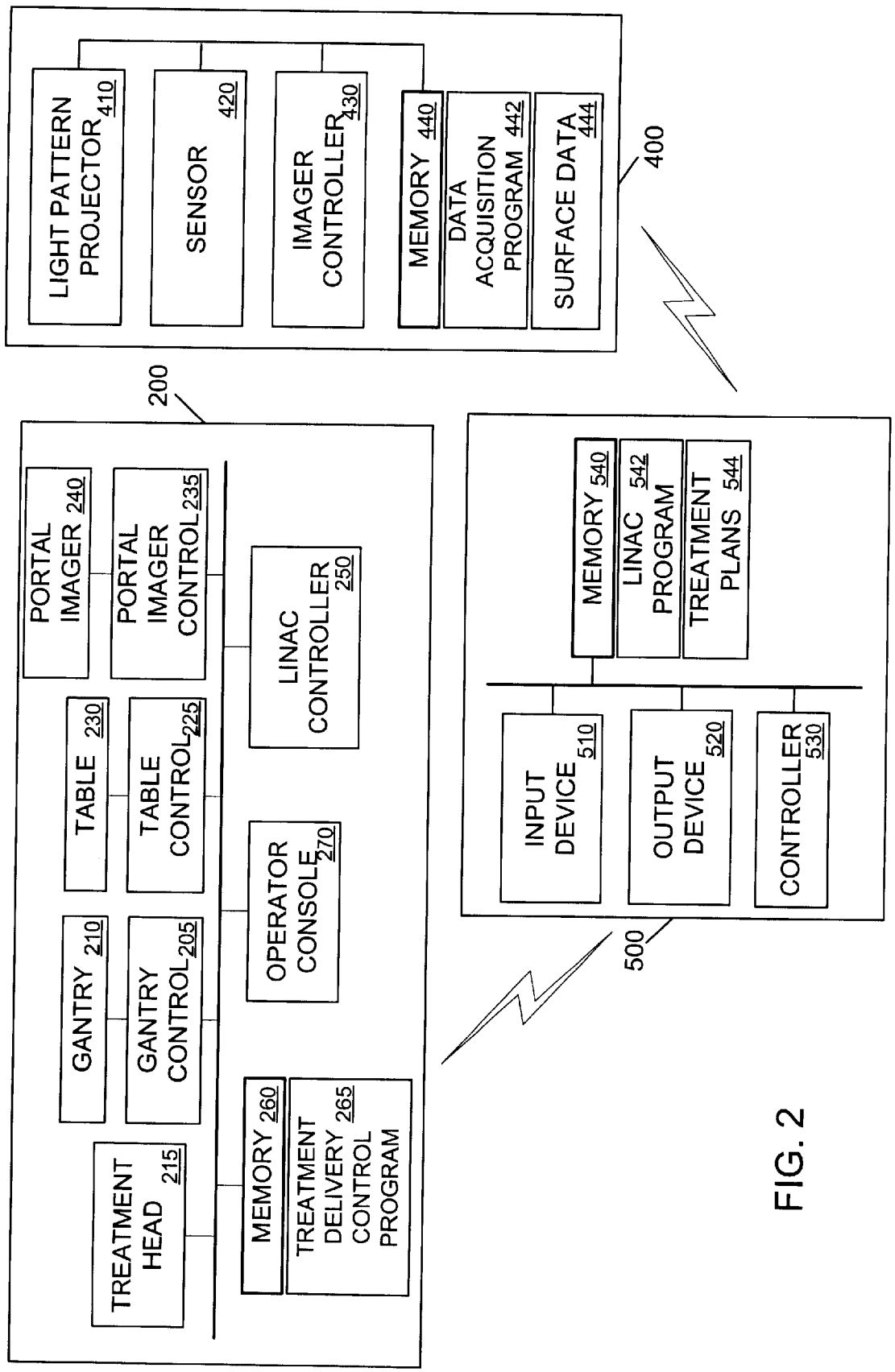
FIG. 2 is a block diagram illustrating elements of devices according to some embodiments of the present invention.

Referring now to FIG. 2, a block diagram is shown depicting portions of Linac 200, surface imager 400 and Linac computer 500. Linac computer 500 is not shown in FIG. 1 because Linac computer 500 is typically operated by a therapist who is located in a different room so as to be protected from radiation. The therapist administers actual delivery of a sequential radiation treatment plan. An extent of manual intervention required from the therapist varies across embodiments of the invention, with some embodiments being capable of automatically executing several successive segments without any intervention.

The therapist operates Linac computer 500 by using input device 510, such as a keyboard or the like. Data can be input from other devices such as Linac 200 and surface imager 400 via an I/O port (not shown). Various data can be output to the therapist before and during treatment via output device 520. U.S. Pat. No. 6,222,544 to Tarr et al. describes a graphical user interface that may be presented to the therapist via output device 520 in order to control the delivery of radiation treatment.

Memory 540 stores data for controlling and generated by Linac 200. This data includes process steps of Linac program 542 which are executed by controller 530 to provide control over Linac 200 so as to execute one of treatment plans 544 defined by an oncologist for a particular patient. One or more of treatment plans 544 may be a sequential treatment plan and may include IMRT or CRT techniques. In some embodiments, one or more of treatment plans 544 are stored in a format suitable for sequential treatment, such as the PRIMEVIEW™ format. These formats specify parameters of successive treatment segments in a manner that can be used by a Linac to deliver the successive segments with little or no operator intervention.

Treatment plans 544 may be generated based on CT data acquired for particular patients and may be transmitted to Linac computer 500 via any type of communication link usable to transmit data. Of course, treatment plans 544 may be generated by Linac computer 500 using Linac program 542.

Among the details specified by treatment plans 544 are surface data and CT data that are used in some embodiments to determine if a patient is correctly positioned according to a sequential radiation treatment plan. This determination is also based on data acquired by surface imager 400 and portal imager 240, and will be described in detail below with respect to FIGS. 5a through 5d.

As shown in FIG. 2, surface imager 400 includes light pattern projector 410, sensor 420, image controller 430 and memory 440. Light pattern projector 410 and sensor 420 are controlled by imager controller 430 to acquire range data representing a three-dimensional surface as described above. Imager controller 430 may exert this control by executing process steps of data acquisition program 442, and may be further controlled based on commands received from Linac computer 500. The commands may be issued in order to automatically control delivery of a treatment segment. For example, after issuing commands to automatically position a patient relative to treatment head 215, Linac computer 500 may command surface imager 400 to acquire data representing a three-dimensional surface of the patient. The data may be used along with data acquired by portal imager 240 to determine if the patient is properly positioned. The acquired surface data may also be stored in memory 440 as surface data 444. Surface data 444 may include several sets of surface data representing portions of different patient's bodies. In some embodiments, surface data 444 includes range data that has been transformed to the coordinate frame of Linac 200.

Radiation treatment is delivered by treatment head 215 under control of Linac controller 250. Particularly, Linac controller 250 executes process steps of treatment delivery control program 265 to generate and deliver a beam of radiation according to a treatment plan such as those stored among treatment plans 544. In this regard, Linac computer 500 may transmit segment parameters to Linac 200, which in turn fulfills those parameters using functions provided by treatment delivery control program 265.

Some of the parameters may require Linac controller 250 to issue a command to gantry control 205 to rotate gantry 210 to a specified position relative to patient 300. Other parameters may cause table control 225 to move table 230 to an appropriate position so as to position patient 300 properly with respect to treatment head 215, and still others may cause portal imager control 235 to reposition portal imager 240. In some embodiments, treatment delivery control program 265 includes process steps of the SIMTEC™ delivery system. The SIMTEC system is capable of interpreting PRIMEVIEW-formatted sequential treatment plans and to automatically execute those plans.

Of course, embodiments of the invention are not limited to automatic control of Linac 200. In this regard, many functions of Linac 200 may be controlled by an operator manually using operator console 270, which may be a hard or wireless-linked remote control device.

Figure 3:
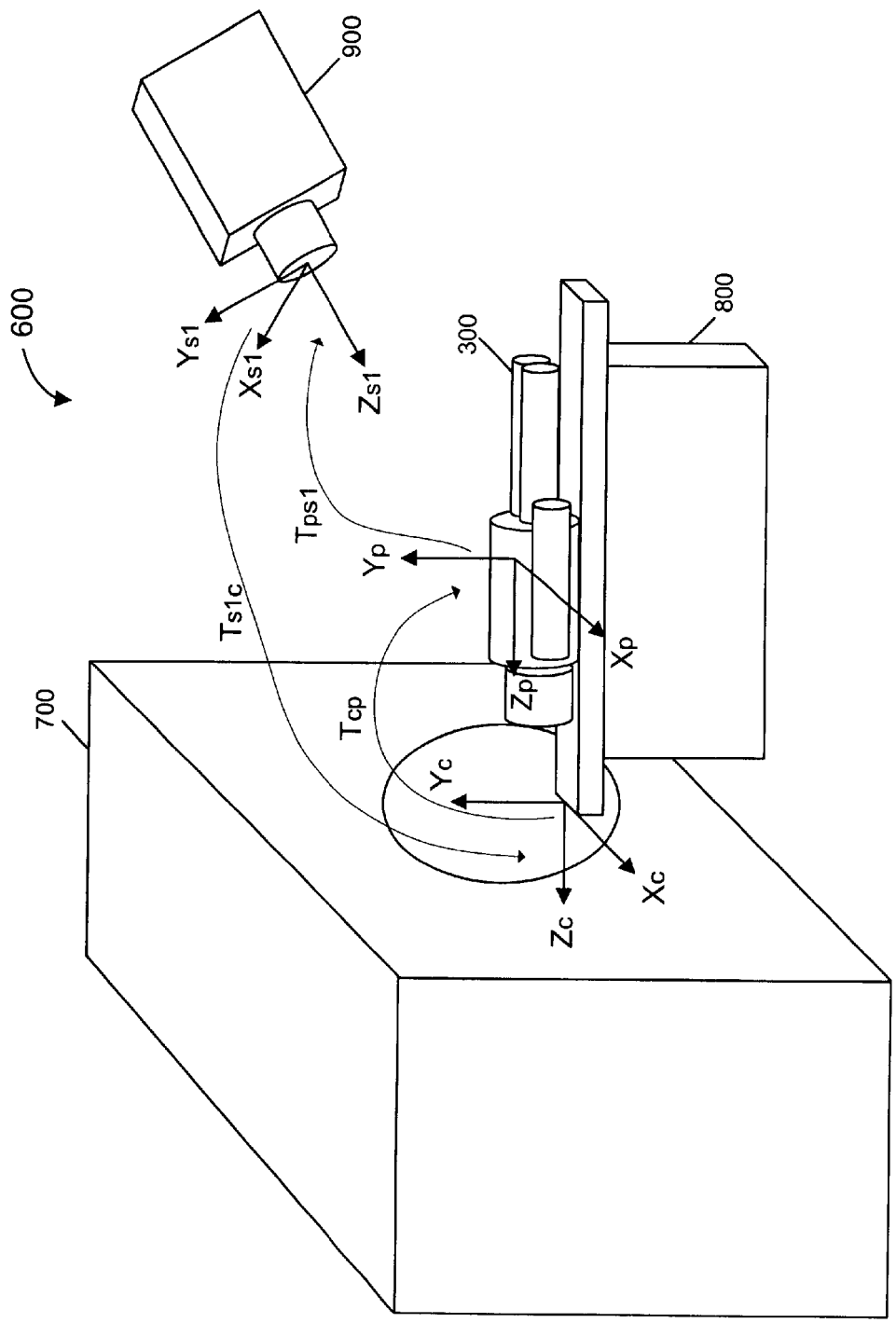
FIG. 3 is a diagram illustrating a CT room according to some embodiments of the present invention.

FIG. 3 illustrates CT room 600 configured to acquire data in accordance with some embodiments of the present invention. CT room 600 includes CT device 700, CT table 800, patient 300, and surface imager 900. As described with respect to FIG. 1, the coordinate axes and the arrows connecting the axes will be ignored until later in the present specification.

CT device 700 is used to obtain CT data representing at least a portion of patient 300. Specifically, CT device acquires CT data by exploiting the x-ray principal: as x-rays pass through the body they are absorbed or attenuated at differing levels, thereby creating a matrix or profile of x-ray beams of different strength. In conventional x-ray imaging, an image of the profile is produced using film that is sensitive to x-rays. In the case of CT, the film is replaced by a banana-shaped detector that measures the x-ray profile and outputs data representing the profile.

The detector is mounted on a rotating frame inside CT device 700. Mounted opposite to the detector is an x-ray tube that emits a fan beam of x-rays as the rotating frame spins the x-ray tube and detector around patient 300. As the x-ray tube and detector spin, the detector measures profiles of the attenuated x-ray beam. Typically, in one 360° spin, about 1,000 profiles are measured. Each profile is subdivided spatially by the detector and fed into about 700 individual data channels. Each profile is then reconstructed into a two-dimensional image of the portion or "slice" of patient 300 that was scanned. The two-dimensional images may be processed to create a three-dimensional image. Both the two-dimensional images and the three-dimensional image are referred to herein as CT data, and both show tissue as well as bone. In some embodiments, the acquired CT data is represented in what will be referred to as a CT coordinate frame, depicted by axes $x_c$, $y_c$, and $z_c$ of FIG. 3.

CT table 800 is used to position a patient before, during and after acquisition of CT data. As such, CT table 800 is capable of moving so as to place relevant portions of the patient 300 in the path of the x-ray beam within CT device 700. This movement may be under the control of an operator and/or a computer program. It should be noted that any currently or hereafter-known CT table and CT device may be used in accordance with the present invention.

Surface imager 900 is used to acquire surface data representing a three-dimensional surface within CT room 600. Surface imager 900 may be identical to surface imager 500, may be a different model of surface imager that utilizes a same operational principle as imager 500, or may be a surface imager operating in an entirely different manner from imager 500. The acquired surface data, which may comprise range data, may be used to determine whether patient 300 is in a proper position for delivery of treatment in Linac room 100. More specifically, surface imager 900 may acquire data representing a surface of patient 300 while patient 300 is in a position that is substantially maintained during acquisition of CT data representing an internal portion of patient 300. Accordingly, prior to delivering a treatment segment based on the CT data in Linac room 100, surface data acquired in CT room 600 is compared with surface data acquired by imager 400 in Linac room 100 to determine if patient 300 is substantially in the same position.

Figure 4:
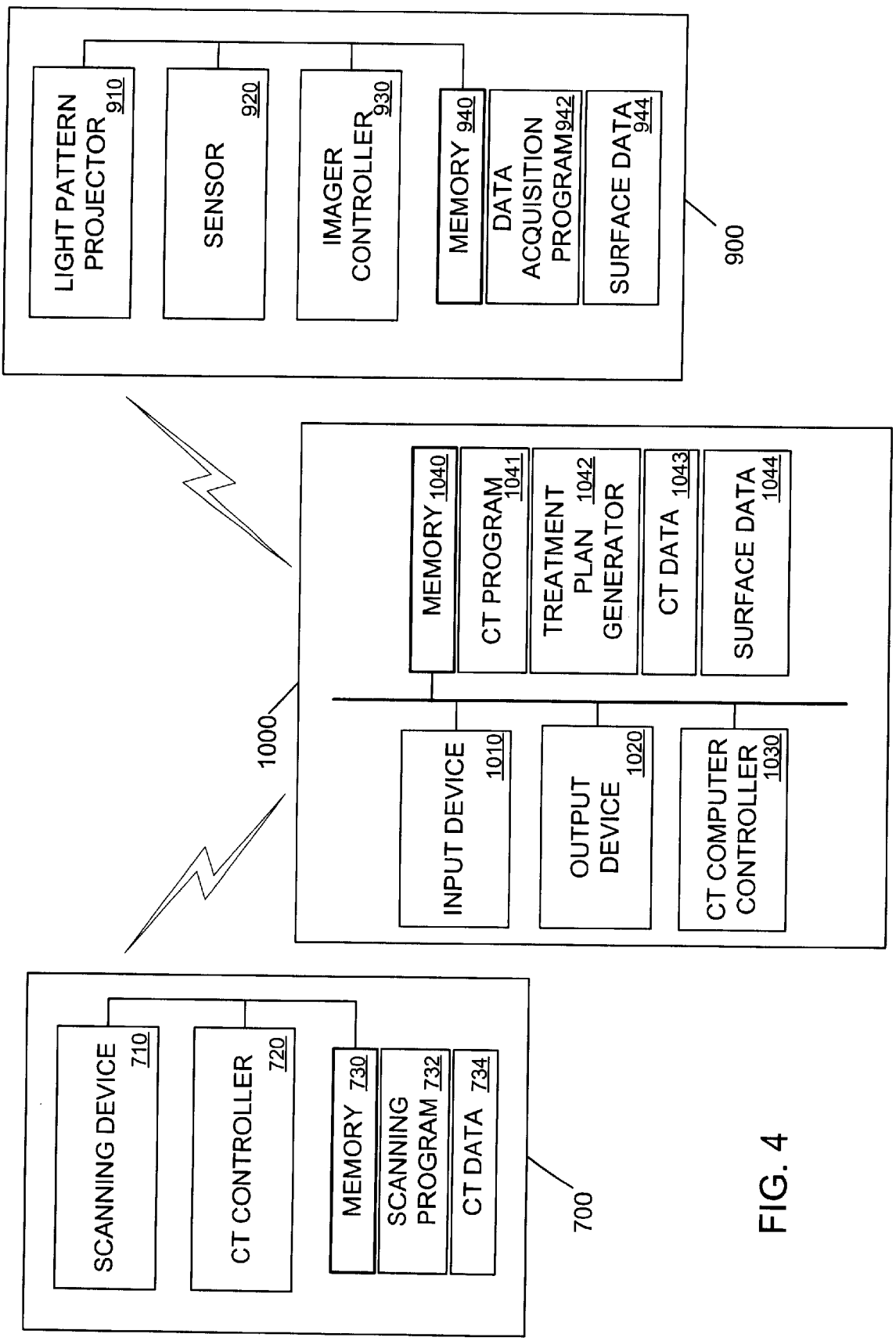
FIG. 4 is a diagram illustrating elements of devices according to some embodiments of the present invention.
Figure 5A:
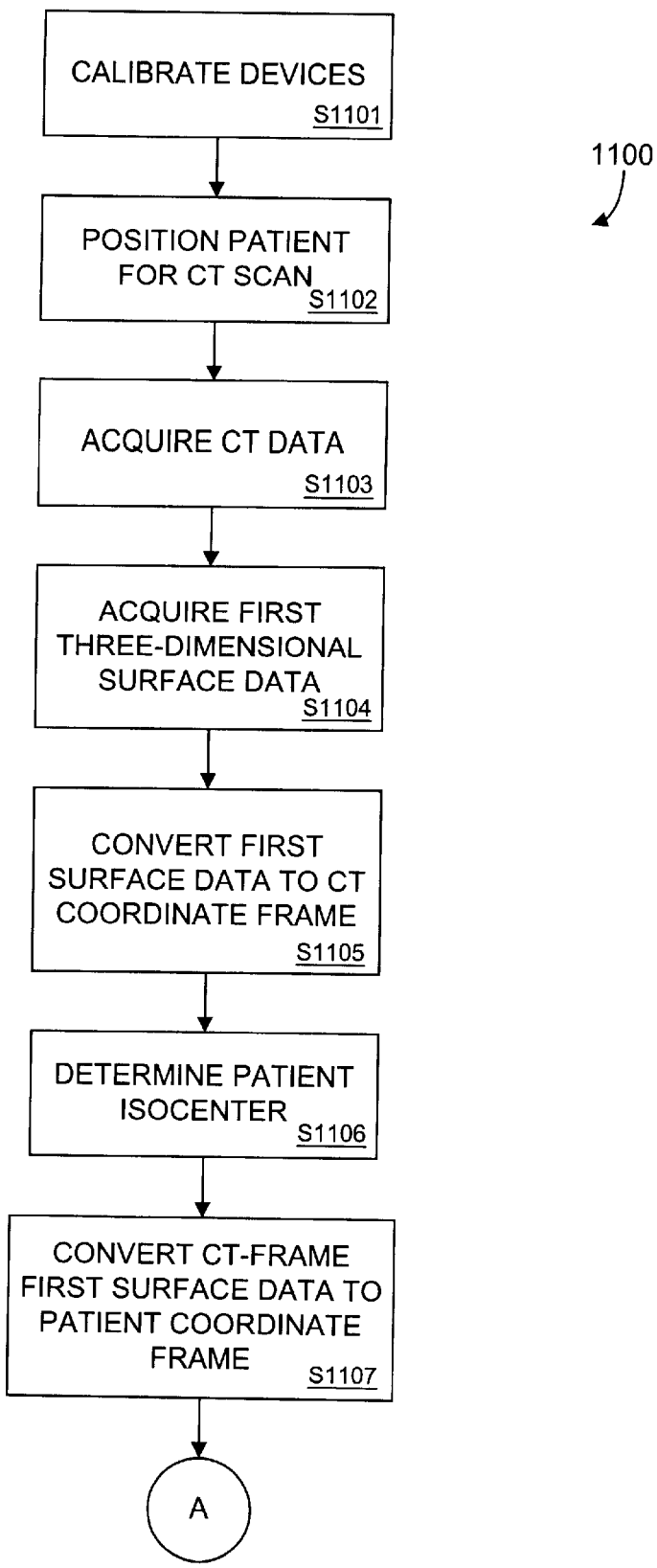
FIGS. 5a through 5d are flow diagrams illustrating process steps for using surface photogrammetry and portal imaging according to some embodiments of the present invention.
Figure 5B:
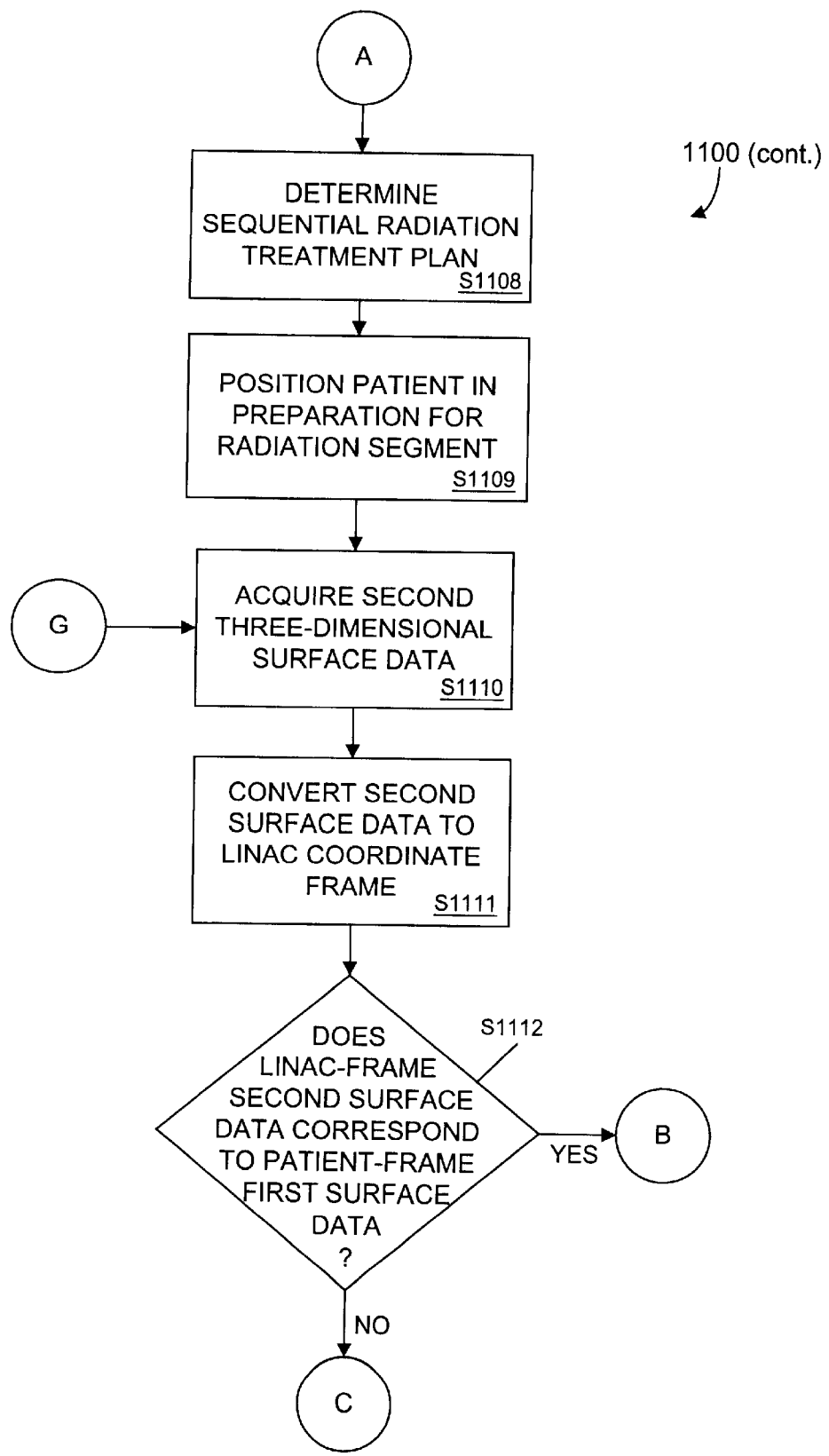
Figure 5C:
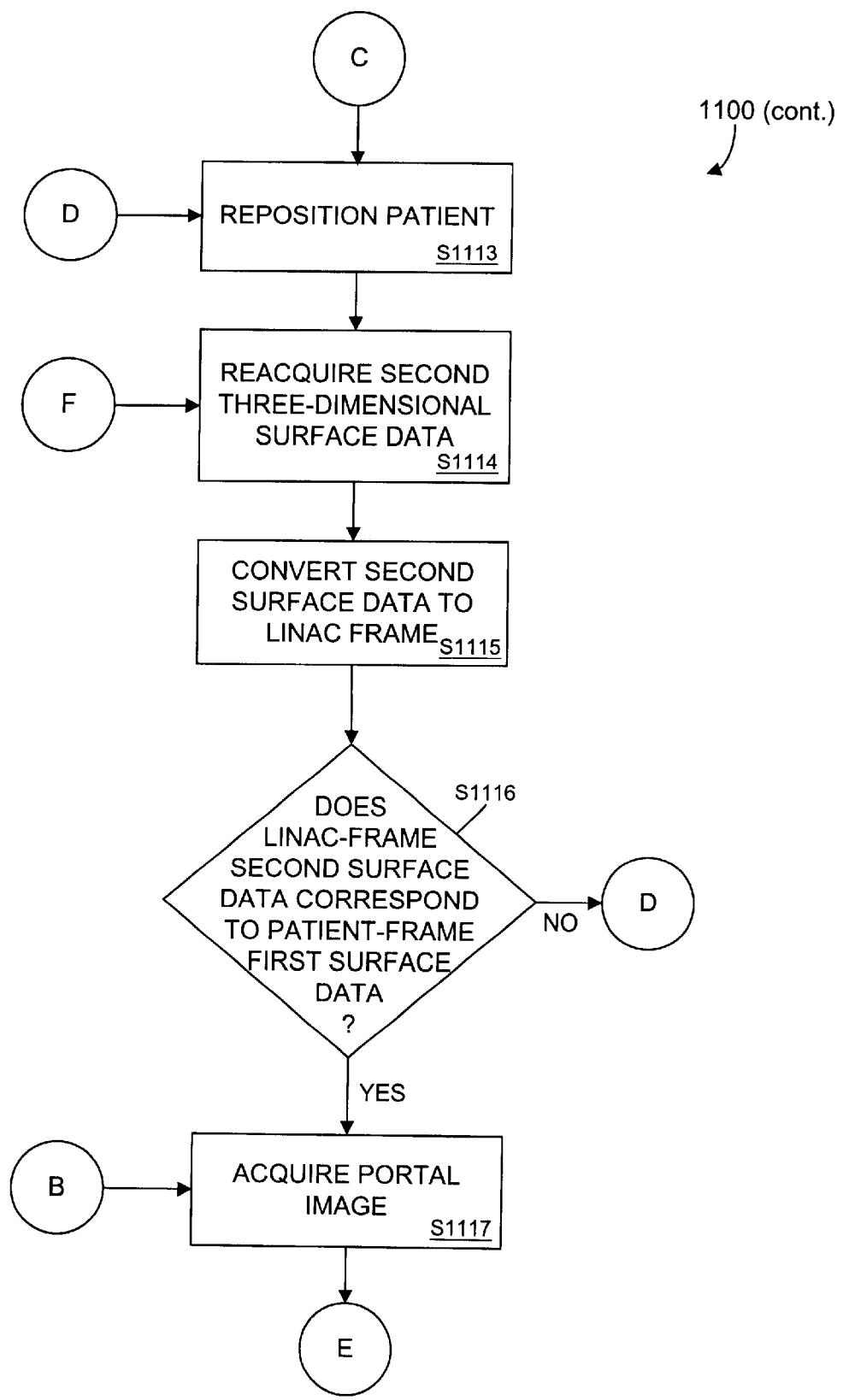
Figure 5D:
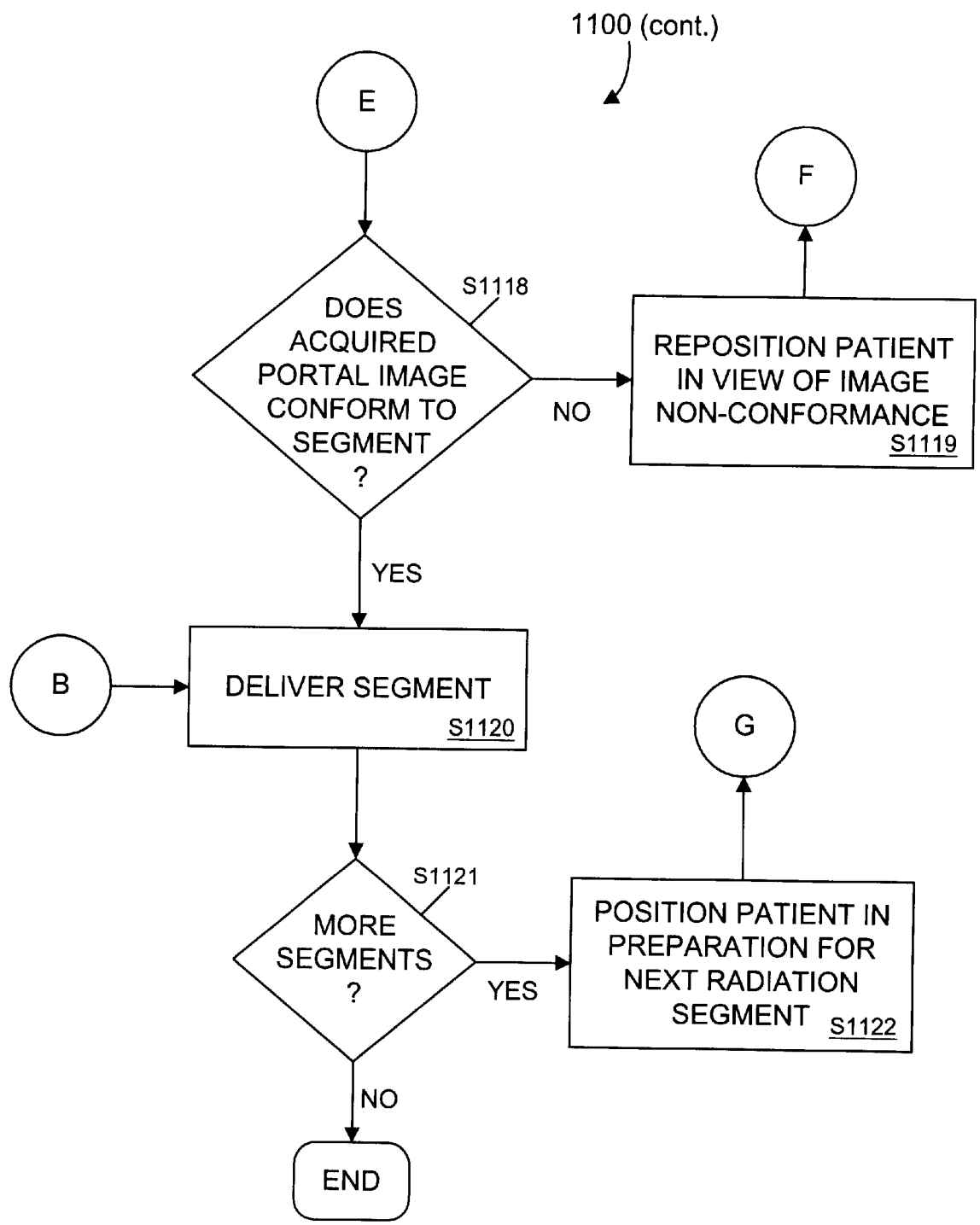

FIG. 4 illustrates internal architectures of various elements of CT room 600, including CT device 700 and surface imager 900. Also illustrated is an internal architecture of CT computer 1000, which is not shown in CT room 600. CT computer 1000 may be operated so as to cause CT device 700 to perform steps in accordance with embodiments of the present invention. CT computer 1000 may be located within CT room 600, in a radiation-proof room adjacent to CT room 600, or elsewhere.

As shown, CT device 700 includes scanning device 710, which includes the x-ray tube and detector described above as well as other physical devices needed to generate x-ray profiles. CT controller 720 controls scanning device 710 using internal logic and/or executable process steps. Accordingly, scanning device 710 may comprise a microprocessor, a programmable logic controller or the like. Some of these process steps may be part of scanning program 732 stored in memory 730. In this regard, scanning program 732 includes executable process steps for controlling the hardware elements of CT device 700 to scan a body and to thereby generate x-ray profiles. The generated x-ray profiles are stored in memory 730 as CT data 734. CT data 734 may include raw profile data, two-dimensional images generated based on raw profile data, and three-dimensional images generated based on raw profile data and/or two-dimensional images.

CT computer 1000 includes input device 1010, output device 1020, CT computer controller 1030, and memory 1040. Input device 1010 may be manipulated by an operator to submit commands to CT computer 1000 and to CT device 700. Input device 1010 may therefore comprise one or more of a keyboard, a pointing device, a touch screen or any other input device. Output device 1020 is used to output images, data and text to the operator, and therefore may comprise a display, a printer, and the like. Data may also be input to and output from CT computer 1000 using a communication port (not shown) that links CT computer 1000 to other devices. For example, commands may be transmitted to and CT data may be received from CT device 700 over such a communication port.

CT computer controller 1030 controls elements of CT computer 1000 according to internal logic and/or executable process steps. The process steps may be received from another device or stored in memory 1040. Process steps used to control the functions of CT device 700 are found in CT program 1041. Treatment plan generator 1042 stores process steps that are executable to generate a sequential radiation treatment plan based on CT data acquired by CT device 700 and on surface data acquired by surface imager 900. In some embodiments, treatment plan generator 1042 includes process steps to produce PRIMEVIEW-formatted sequential treatment plans that may be used to automatically deliver successive treatment segments.

Also stored in memory 1040 are CT data 1043 and surface data 1044. CT data 1043 merely includes CT data generated by CT device 700 in any format, including raw and/or image format. In some embodiments, the data of CT data 1043 is represented in the coordinate frame of CT device 700. Surface data 1044 includes three-dimensional surface data generated by surface imager 900, formatted in one or more of the coordinate frame of imager 900, of CT device 700, or of patient 300. Conversion between the various coordinate frames is set forth below.

Surface imager 900 in the present example is identical to surface imager 400 and a discussion of its physical elements will therefore be omitted. However, it should be noted that surface imager 900 acquires data representing a three-dimensional surface of patient 300 while in a position substantially maintained during a CT scan.

Of course, each of the devices shown in FIGS. 2 and 4 may include less or more elements than those shown. Moreover, transformation and storage of acquired data may be performed by any one or more of the devices. In addition, embodiments of the invention are not limited to the three devices shown in the figures.

FIGS. 5*a* through 5*d* illustrate process steps 1100 according to some embodiments of the present invention. Process steps 1100 may be performed by various devices under the control of controller-executable process steps stored locally to the devices or received from other devices. The following description of process steps 1100 associates each process step with a device that performs the step, and also mentions two or more alternative devices for performing some process steps. Of course, embodiments of the present invention may differ from the description of process steps 1100. In addition, the particular arrangement of process steps 1100 are not meant to imply a fixed order to the steps; embodiments of the present invention can be practiced in any order that is practicable.

Initially, in step S1101, CT device 700 and surface imager 900 are calibrated. As shown in FIG. 3, CT device 700 acquires CT data that is represented in a coordinate frame illustrated by axes $X_c$, $Y_c$ and $Z_c$. This coordinate frame will be referred to as the CT frame. Surface imager 900 acquires three-dimensional surface data formatted with respect to a coordinate frame illustrated by axes $X_{s1}$, $Y_{s1}$ and $Z_{s1}$. Calibration consists of determining a transformation matrix $T_{s1c}$ for converting data represented in the coordinate frame of imager 900 to data represented in the CT frame.

Figure 6:
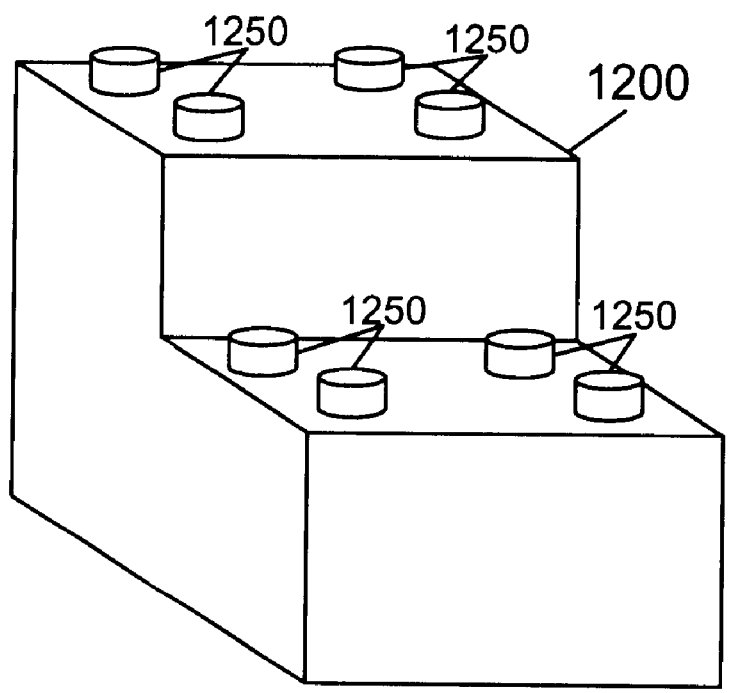
FIG. 6 is a view of a phantom used to calibrate a system according to embodiments of the present invention.

FIG. 6 illustrates phantom 1200 used to determine transformation matrix $T_{s1c}$ according to some embodiments of step S1101. The body of phantom 1200 consists of a material with a low x-ray absorption coefficient, such as acrylic. Phantom 1200 includes eight fiducial markers 1250 that may be sensed by CT device 700 as well as by surface imager 900, and which possess an x-ray absorption coefficient that is relatively higher than the body's coefficient.

More specifically, phantom 1200 is placed at the intersection of axes $X_c$, $Y_c$ and $Z_c$ while CT table 800 is at the zero position shown in FIG. 3. Phantom 1200 is then scanned by CT device 700, thereby generating CT data represented in the CT frame. Table 800 is returned to the zero position and surface imager 900 acquires three-dimensional surface data representing phantom 1200. Because they extend from the body of phantom 1200, the acquired data will represent fiducial markers 1250. Coordinates of eight points representing markers 1250 are identified from each of the CT data and the surface data. The coordinates are used to generate an over-determined set of linear equations, the solution of which is $T_{s1c}$. Preferably, phantom 1200 includes at least four non-coplanar corresponding points that may be used to solve for $T_{s1c}$ using known matrix techniques. $T_{s1c}$ may be stored in memory 1040 of CT computer 1000. In this regard, step S1101 may be performed by CT device 700 and surface imager 900 under control of CT computer 1000.

Step S1101 also includes calibration of Linac 200 and surface imager 400. This calibration is intended to produce transformation matrix $TS_{s2L}$, which may be used to convert data acquired by surface imager 400 to a coordinate space of data acquired by Linac 200.

Linac table 230 is initially moved to its zero position as shown in FIG. 1. FIG. 1 also shows coordinate axes $X_L$, $Y_L$ and $Z_L$ representing a Linac coordinate frame and axes $X_{s2}$, $Y_{s2}$ and $Z_{s2}$ representing a coordinate frame of surface imager 400. Phantom 1200 is placed at the origin of the Linac coordinate frame and surface imager 400 acquires data representing a three-dimensional surface of phantom 1200. Coordinates of fiducial markers 1250 are extracted from the acquired data.

Next, Linac table 230 is moved so as to position one of markers 1250 at the isocenter of Linac 200. The isocenter is a point to which a radiation would be focused if Linac were activated. In FIG. 1, the isocenter lies at the origin of the Linac coordinate frame. The coordinates of Linac table 230 are recorded and table 230 is moved so as to position another of markers 1250 at the isocenter of Linac 200. Again the coordinates of table 230 are recorded. The above process is repeated for each of markers 1250. As described with respect to $T_{s1c}$, the eight coordinates acquired by surface imager 400 and the eight table coordinates are used to generate an over-determined set of linear equations, the solution of which is $T_{s2L}$.

Of course, the phantoms used to calibrate in CT room 600 and in Linac room 100 need not be identical. Moreover, embodiments of the invention may utilize methods of determining each of the transformation matrices that are different than that described above.

Flow continues from step S1101 to step S1102, in which a patient is positioned for a CT scan in CT room 700. The patient's body is positioned on CT table 800 in a manner intended to produce a best-quality CT data of a specific internal portion of the patient. Such positioning may require the creation and/or use of pillows, wedges, supports or shields. Once the patient is adequately positioned, CT device 700 acquires CT data in step S1103 as described above. The acquired CT data is stored among CT data 734 and CT data 1043, and is represented in the CT coordinate frame.

In step 31104, surface imager 900 executes data acquisition program 942 to acquire data representing a three-dimensional surface of the patient's body. The three-dimensional surface is intended to substantially mimic a surface of the patient's body and other physical elements as positioned during acquisition of the CT data. Accordingly, it may be beneficial to perform step S1104 contemporaneously with step S1103.

The surface data is stored among surface data 944 and is represented in the coordinate frame of imager 900. Accordingly, the surface data is converted to the CT coordinate frame in step S1105. In the present embodiment, the conversion is performed by CT computer 1000, which executes CT program 1041 to apply transformation matrix $T_{s1c}$ to the surface data. The converted data is then stored among surface data 644.

Next, a patient isocenter is determined in step S1106. The isocenter is a point within the patient's body on which a radiation beam should be focused according to a treatment plan. Accordingly, a position of the isocenter is determined by a specialist who examines graphic representations of the CT data acquired in step S1103. The representations may be displayed by output device 1020 and/or may be presented by output device 1020 in hardcopy form. It should be noted that, according to this embodiment, steps S1103 through S1106 may be performed in any order, as long as step S1103 occurs prior to step S1106, and step S1104 occurs prior to step S1105.

It will be assumed that the patient isocenter is determined to be located at the intersection of axes $X_p$, $Y_p$ and $Z_p$ of FIG. 3. Using the coordinates of the isocenter with respect to the CT coordinate frame, the CT-frame surface data is converted in step S1107 to the coordinate frame defined by axes $X_p$, $Y_p$ and $Z_p$, or the patient coordinate frame. The conversion may be performed by CT computer 1000, and the converted data may be stored among surface data 1044.

A sequential radiation treatment plan is determined in step S1108 based on the acquired CT data, the acquired surface data and on data representing a physical layout of a radiation treatment station. The latter data may be stored in memory 1044 of CT computer 1000, and includes models of gantry 210, base 220, Linac table 230 and of any other element that may physically interfere with patient 300 during radiation treatment. The treatment plan may be determined by operating CT computer 1000 to execute treatment plan generator 1042.

In some embodiments of step S1108, one or more specialists view superimposed representations of the CT data, the surface data and the physical layout data to determine how best to treat tissue located at the determined patient isocenter. In order to simplify processing required by CT computer 1000 to superimpose the representations, the surface data may be represented in the CT coordinate frame. Of course, treatment plan generator may include executable process steps to generate such a scenario using surface data represented in the coordinate frame of imager 900.

The sequential treatment plan may include parameters of a treatment including a plurality of fractions, with each fraction including a plurality of segments. For each segment, the plan may specify parameters including gantry position, table position, beam shape, beam type, beam intensity, patient surface position, portal view, etc. The plan may also or alternatively include scripts executable by Linac controller 250 to automatically deliver a segment according to the parameters. As described above, the plan may be generated in PRIMEVIEW format to enable execution by a SIMTEC-enabled Linac. The determined sequential treatment plan may be transmitted to Linac computer 500 for storage among treatment plans 544.

In step S1109, patient 300 is positioned on Linac table 230 in preparation for a first segment of a first fraction of the treatment plan. In some embodiments, patient 300 is positioned so that laser beams emitted from devices mounted in Linac room 100 intercept tattoos or other markings placed on the patient in CT room 700. According to some of these embodiments, a patient's body is marked at three or more points orthogonal to the determined isocenter. To mark the patient thusly, the patient is positioned on CT table 800 and CT computer 1000 uses coordinates of the determined isocenter to position beam-emitting devices (not shown) orthogonal to the isocenter. The patient is then marked where the beams intercept the patient's body. In Linac room 100, beam-emitting devices are mounted such that their emitted beams would intersect at the isocenter of Linac 200 if the beams intercepted the tattoos. Other conventional techniques may be used to position patient 300 in step S1109.

Surface imager 400 acquires data representing a three-dimensional surface of at least a portion of patient 300 in step S1110. The acquired data is represented in the coordinate frame of imager 400 and stored among surface data 444. Next, in step S1111, Linac computer 500 converts the data acquired in step S1110 to the Linac coordinate frame using transformation matrix $T_{s2L}$. The converted data may be stored in memory 540.

In step S1112, Linac computer 500 executes Linac program 542 to determine if the surface data produced in step S1111 corresponds to the surface data produced in step S1107. The data may be determined to correspond if the coordinates reflected in the data are identical or vary by less than a specified statistical, mathematical or distance threshold. The determination may only take into account surface data reflecting portions of patient 300 that lie within a certain distance of the Linac isocenter, and may include manual as well as automated steps. Since the surface data produced in step S1111 is represented in the Linac coordinate frame and the surface data produced in step S1107 is represented in the patient coordinate frame, determination of a correspondence in step S1112 indicates that the patient isocenter is located substantially at the Linac isocenter and that a relevant surface of patient 300 is substantially at the same position as it was in step S1104.

The data comparison of step S1112 will be simplified if patient 300 is positioned in step S1109 so that the patient isocenter is located substantially at the Linac isocenter. In such a case, the sets of data may be directly compared since the data are represented in substantially identical coordinate frames. Of course, conventional data analysis techniques may be used to register the two sets of data in a same coordinate frame prior to comparing the data.

If the determination in step S1112 is positive, flow would then proceed to step S1117, which will be described shortly. If the data are determined not to correspond, then the patient isocenter is not located substantially at the Linac isocenter, a relevant surface of patient 300 is not substantially at the same position as it was in step S1104, or both. Flow therefore continues to step S1113, wherein patient 300 is repositioned.

Repositioning in step S1113 may include any method of changing a position of patient 300 relative to Linac treatment head 215, including one or more of instructing patient 300 to move, physically moving patient 300, rotating gantry 210, moving Linac table 230, and moving portal imager 240. It may be necessary to move portal imager 240 in order to rotate gantry 210 or move table 230 without physically interfering therewith. In some embodiments, the execution of scripts of the determined sequential treatment plan directly by Linac controller 250 or through treatment delivery program 265 provides for automatic repositioning of patient 300 by controlling gantry 210, table 230 and portal imager 240 if it is determined that patient 300 is positioned incorrectly. Automatic repositioning may be based on analyzed differences between the Linac-frame surface data and the patient-frame surface data.

Some or all repositioning steps may be accomplished manually by an operator using operator console 270 or input device 510. The operator may be guided by instructions determined based on the analyzed differences and presented through console 270 or output device 520. In some embodiments, the operator is presented with an image representing the patient-frame surface data superimposed on an image representing the Linac-frame surface data. As the patient is repositioned, the Linac-frame data is periodically re-acquired and the superimposed image representing the surface of patient 300 in Linac room 100 is periodically updated based on the re-acquired data.

Surface imager 400 acquires second data representing a three-dimensional surface of a portion of the body of patient 300 in step S1114. The second data is converted to the Linac coordinate frame in step S1115 in the manner described above with respect to step S1111. Then, in step S1116, it is determined whether the converted second surface data corresponds to the patient-frame surface data generated in step S1107. This determination may be performed using any of the techniques discussed with respect to step S1112. If the determination is negative, flow returns to step S1113 and continues therefrom. If it is determined that the converted second surface data corresponds to the patient-frame surface data, a portal image is acquired in step S1117.

A portal image is acquired by causing portal imager control 235 to position portal imager 240 in a position where the patient isocenter lies between portal imager 240 and treatment head 215. Treatment head 215 then emits x-ray photons that are sensed by portal imager 240 to acquire an image. According to some embodiments of the present invention, Linac controller 250 and portal imager control 235 perform processing to enhance or manipulate the acquired image. Next, in step S1118, the acquired image is analyzed to determine if it conforms to a portal image associated with the current treatment segment. CT data that was used to generate the segment may be used in the analysis of step S1118. In some embodiments, steps S1117 and S1118 are performed automatically by executing scripts of the treatment plan. Steps S1117 and S1118 may also be performed automatically based on steps of treatment delivery control program 265, which simply receives segment parameters including surface data and CT data and performs process steps 1100 based thereon.

If the acquired portal image is determined not to conform to the segment, patient 300 is repositioned in step S1119. The repositioning preferably takes into account the non-conformance detected in step S1118. One suitable method for such repositioning is described by Girouard et al. in "Automatic setup deviation measurements with electronic portal images for pelvic fields", Medical Physics, Vol. 25, No. 7, July 1998 Part 1, the contents of which are incorporated by reference herein for all purposes. After repositioning in step S1119, flow returns to step S1114.

If the portal image is determined to conform to the segment in step S1118, the segment is delivered to patient 300 in step S1120. Specifically, Linac 200 delivers a radiation beam of a shape, type, duration and intensity specified by the treatment plan to the patient isocenter (which is substantially identical to the Linac isocenter after performance of process steps 1100). After the segment is delivered, it is determined whether more segments of the current fraction exist. If so, patient 300 is positioned in preparation for the next segment in step S1122 as described above with respect to step S109. Flow then returns to step S1110.

If no more segments exist for the current fraction, process steps 1100 terminate. Of course, if the determined treatment plan includes additional fractions, patient 300 returns to Linac room 100 at a later date to receive treatment. Process steps 1100 may be repeated on such a date, with or without step S1101, which may be performed periodically and not prior to each performance of steps S1102 through S1122.

Those in the art will appreciate that various adaptations and modifications of the above-described embodiments can be configured without departing from the scope and spirit of the invention. For example, after a negative determination in step S1112 and/or an affirmative determination in step S1118, parameters of the treatment segment may be altered as an alternative to repositioning patient 300. In other words, the segment may be modified to take into account differences between the patient-frame surface data acquired in CT room 700 and the Linac-frame surface data acquired in Linac room 100 and/or the non-conformance of the portal image with the CT data. After modifying the segment, the segment may be delivered without repositioning patient 300.

Moreover, it should be noted that functions ascribed to one device herein may be performed by other devices. In one example, the functions ascribed to Linac computer 500 and to CT computer 1000 are performed by a single computing device. In other examples, elements or functions described with respect to one of these devices are present or performed by the other. In this regard, the functions described herein as being performed by one of Linac computer 500 and CT computer 1000 may be performed by a single device or by other devices including Linac 200, surface imager 400, CT device 700 and surface imager 900. Those skilled in the art will also appreciate that any suitable general-purpose or specially-programmed computer may be used to achieve the functionality described herein.

Therefore, it is to be understood that, within the scope of the appended claims, the invention may be practiced other than as specifically described herein.

What is claimed is:

1. A method comprising:

acquiring first data representing a three-dimensional surface of at least a portion of a patient's body while the patient is in a first position substantially maintained in preparation for radiation treatment;

acquiring an image of a first internal portion of the patient's body while the patient is substantially in the first position; and determining if the patient is properly positioned for radiation treatment based on the first data and the image.

2. A method according to claim 1, wherein the step of acquiring the image comprises:

controlling a radiation treatment device to emit photons toward the second internal portion of the patient's body.

3. A method according to claim 2, further comprising:

controlling the radiation treatment device to deliver a radiation treatment plan to the patient's body.

4. A method according to claim 1, further comprising:

acquiring, prior to acquiring the first data, second data representing a three-dimensional surface of at least a portion of the patient's body while the patient is in a second position; and wherein the determining step comprises:

determining if the patient is properly positioned for radiation treatment based on the first data, the second data and the image.

5. A method according to claim 4, further comprising:

acquiring, prior to acquiring the first data, third data representing at least one internal portion of the patient's body while the patient is in the second position; and determining the radiation treatment based on the second data and the third data.

6. A method according to claim 4, further comprising:

determining, based on the first data and the second data, that the second position does not correspond to the first position.

7. A method according to claim 1, further comprising:

acquiring, prior to acquiring the first data, third data representing at least one internal portion of the patient's body while the patient is in a second position; and determining the radiation treatment plan based on the third data.

8. A method according to claim 1, wherein the determining step comprises:

retrieving a stored sequential radiation treatment plan including second data representing a three-dimensional surface of at least a portion of the patient's body in a second position, the second position being a position in which data representing at least an internal portion of the patient's body was acquired; and automatically determining if the patient is properly positioned based on the first data, the second data and the image.

9. A method according to claim 8, wherein if it is determined that the patient is not properly positioned, the first position is automatically changed relative to a radiation treatment device based on the first data, the second data and the image.

10. A method according to claim 1, further comprising:

automatically delivering a first segment of a sequential radiation treatment plan to the patient;

after the first segment is delivered, automatically adjusting a position of the patient relative to a radiation treatment device according to the sequential radiation treatment plan;

automatically adjusting a delivery configuration of the radiation treatment device according to the sequential radiation treatment plan; and automatically delivering a second segment of the sequential radiation treatment plan to the patient.

11. A method according to claim 10, wherein the position of the patient is automatically adjusted based on data representing a second three-dimensional surface of the patient in the position and on a second image of an internal portion of the patient in the position.

12. A method according to claim 11, wherein the position of the patient is automatically adjusted based on second data representing a three-dimensional surface of at least a portion of the patient's body in a third position, the third position being a position in which data representing at least an internal portion of the patient's body was acquired.

13. A method comprising:

acquiring computed tomography data of a patient while the patient remains substantially in a first position;

acquiring first data representing a three-dimensional surface of the patient while the patient remains substantially in the first position;

acquiring second data representing a three-dimensional surface of the patient while the patient remains substantially in a second position with respect to a radiation treatment device;

acquiring an image of a first internal portion of the patient's body while the patient is substantially in the second position; and determining if the second data corresponds to the first data;

determining if the image corresponds to a radiation treatment plan; and delivering radiation to the patient according to the radiation treatment plan.

14. A method according to claim 13, further comprising:

automatically repositioning the patient with respect to the radiation treatment device if it is determined that the second data does not correspond to the first data, and/or if it is determined the image does not corresponds to a radiation treatment plan.

15. A method according to claim 13, further comprising:

automatically repositioning the patient with respect to the radiation treatment device according to the radiation treatment plan;

acquiring third data representing a three-dimensional surface of the patient while the patient remains substantially in a third position at the radiation treatment station;

acquiring an image of a second internal portion of the patient's body while the patient is substantially in the third position; and determining if the third data and the image correspond to the radiation treatment plan; and delivering a second segment of radiation to the patient according to the radiation treatment plan.

16. A medium storing controller-executable process steps, the process steps comprising:

a step to acquire first data representing a three-dimensional surface of at least a portion of a patient's body while the patient is in a first position substantially maintained in preparation for radiation treatment;

a step to acquire an image of a first internal portion of the patient's body while the patient is substantially in the first position; and a step to determine if the patient is properly positioned for radiation treatment based on the first data and the image.

17. A medium according to claim 16, the process steps further comprising:

a step to acquire, prior to acquiring the first data, second data representing a three-dimensional surface of at least a portion of the patient's body while the patient is in a second position; and wherein the determining step comprises:

a step to determine if the patient is properly positioned for radiation treatment based on the first data, the second data and the image.

18. A medium according to claim 17, the process steps further comprising:

a step to acquire, prior to acquiring the first data, third data representing at least one internal portion of the patient's body while the patient is in the second position; and a step to determine the radiation treatment based on the second data and the third data.

19. A medium according to claim 16, wherein the determining step comprises:

a step to retrieve a stored sequential radiation treatment plan including second data representing a three-dimensional surface of at least a portion of the patient's body in a second position, the second position being a position in which data representing at least an internal portion of the patient's body was acquired; and a step to automatically determine if the patient is properly positioned based on the first data, the second data and the image.

20. A medium according to claim 19, wherein if it is determined that the patient is not properly positioned, the first position is automatically changed relative to a radiation treatment device based on the first data, the second data and the image.

21. A medium according to claim 16, the process steps further comprising:

a step to automatically deliver a first segment of sequential radiation treatment plan to the patient;

a step to, after the first segment is delivered, automatically adjust a position of the patient relative to a radiation treatment device according to the sequential radiation treatment plan;

a step to automatically adjust a delivery configuration of the radiation treatment device according to the sequential radiation treatment plan; and a step to automatically deliver a second segment of the sequential radiation treatment plan to the patient.

22. A system comprising:

a surface imager for acquiring first data representing a three-dimensional surface of at least a portion of a patient's body while the patient is in a first position substantially maintained in preparation for radiation treatment;

a portal imager for acquiring an image of a first internal portion of the patient's body while the patient is substantially in the first position; and a computing device for determining if the patient is properly positioned for radiation treatment based on the first data and the image.

23. A system according to claim 22, further comprising:

a second surface imager for acquiring, prior to acquisition of the first data, second data representing a three-dimensional surface of at least a portion of the patient's body while the patient is in a second position, wherein the computing device determines if the patient is properly positioned based on the first data, the second data and the image.

24. A system according to claim 23, further comprising:

a CT device for acquiring, prior to acquisition of the first data, third data representing at least one internal portion of the patient's body while the patient is in the second position; and a second computing device for determining the radiation treatment based on the second data and the third data.

25. A system according to claim 22, further comprising:

a memory storing second data representing a three-dimensional surface of at least a portion of the patient's body in a second position, the second position being a position in which data representing at least an internal portion of the patient's body was acquired, and wherein the computing device automatically determines if the patient is properly positioned based on the first data, the second data and the image.

26. A system according to claim 25, wherein if it is determined that the patient is not properly positioned, the computing device controls a radiation treatment device to automatically change the position of the patient relative to the radiation treatment device based on the first data, the second data and the image.

* * * * *